United States Patent [19]
Arnold et al.

[11] 4,147,868
[45] Apr. 3, 1979

[54] ACETYLENE-SUBSTITUTED AROMATIC BENZILS AND ACETYLENE-TERMINATED QUINOXALINE COMPOSITIONS

[75] Inventors: Fred E. Arnold, Centerville; Frederick L. Hedberg, Dayton, both of Ohio

[73] Assignee: The United States of America as represented by the Secretary of the Air Force, Washington, D.C.

[21] Appl. No.: 870,705

[22] Filed: Jan. 19, 1978

Related U.S. Application Data

[62] Division of Ser. No. 762,078, Jan. 24, 1977, Pat. No. 4,098,825.

[51] Int. Cl.$^2$ .................. C07D 241/44; C07D 241/42
[52] U.S. Cl. ..................................... 544/353; 544/354
[58] Field of Search .................... 260/250 Q; 544/353, 544/354

[56] References Cited

U.S. PATENT DOCUMENTS 3,966,729   6/1976   Kovar et al. ..................... 260/250 Q Primary Examiner—Mark L. Berch
Attorney, Agent, or Firm—Joseph E. Rusz; Cedric H. Kuhn

[57] ABSTRACT

Acetylene-terminated quinoxaline compositions are prepared by reacting an aromatic bisbenzil with an excess of a bis(o-diamine) to provide an ortho-diamino endcapped quinoxaline oligomer which is then converted to the acetylene endcapped composition by reacting with an acetylenic benzil.

6 Claims, No Drawings

ACETYLENE-SUBSTITUTED AROMATIC BENZILS AND ACETYLENE-TERMINATED QUINOXALINE COMPOSITIONS

RIGHTS OF THE GOVERNMENT

The invention described herein may be manufactured and used by or for the Government of the United States for all governmental purposes without the payment of any royalty.

This is a division of application Ser. No. 762,078, filed Jan. 24, 1977, and issued on July 4, 1978, as U.S. Pat. No. 4,098,825.

FIELD OF THE INVENTION

This invention relates to acetylene-substituted aromatic benzils and to a method for their preparation. In one aspect, it relates to acetylene-terminated quinoxaline compositions.

BACKGROUND OF THE INVENTION

The acetylene-terminated polyphenylquinoxalines, disclosed in U.S. Pat. No. 3,966,729, are one of the most promising new matrix resins for advanced aircraft and aerospace systems. The materials propagate and cure by addition reactions to form high molecular weight, thermally stable compositions. The addition process obviates all problems associated with volatile by-product formation that occurs when such materials are prepared by the normal condensation process. The new resins demonstrate an excellent potential for use as matrices in high performance structural composites.

The principal drawback in the acetylene-terminated quinoxaline system disclosed in the aforementioned patent is the difficulty in working with the very unstable 4-(3-ethynylphenoxy)orthophenylene diamine utilized as the oligomer endcapping agent. Because of the susceptibility of the endcapping agent to oxidation, it cannot be isolated and stored for any length of time. As a result, the resins prepared with the agent are very costly, an important factor in selecting resins for use as composite matrices.

It is a principal object of this invention, therefore, to provide improved acetylene-containing endcapping agents that overcome the shortcomings of the agent disclosed in the aforementioned patent.

Another object of the invention is to provide a process for preparing the acetylene-containing endcapping agents.

A further object of the invention is to provide improved acetylene-terminated phenylquinoxaline oligomers which exhibit low softening points, thereby making such materials more amenable to composite fabrication.

Still another object of the invention is to provide a process for preparing the acetylene-terminated phenylquinoxaline oligomers.

Other objects and advantages of the invention will become apparent to those skilled in the art upon consideration of the ensuing disclosure.

SUMMARY OF THE INVENTION

The present invention resides in acetylene-substituted aromatic benzils as represented by the following formula:

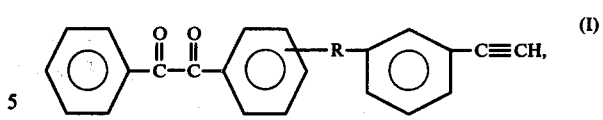

wherein R is oxygen or sulfur and R is ortho, meta or para to the carbonyl functionality.

The acetylene-containing aromatic benzils having the foregoing formula are prepared by the nucleophilic displacement reaction of a nitro leaving group of a benzil (IV) with a metallic salt of an ethynyl-substituted phenol or thiophenol (III). The metallic salt is generated from the base hydrolysis of the corresponding tosylated phenol or thiophenol (II). The reactions involved are shown by the equations set forth below in which the Roman numerals refer to the compounds indicated in the preceding sentences and the Roman number (I) designates the acetylene-containing aromatic benzils.

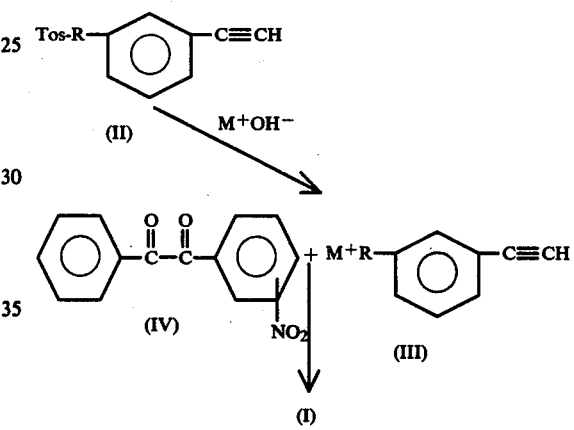

In the above equations, Tos is

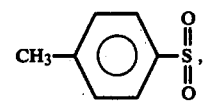

R is oxygen or sulfur, and M is an alkali metal, such as potassium or sodium. The materials used in synthesizing the acetylenic benzils (I) are well known compounds that are described in the literature. The acetylenic benzils are stable to both air and light so that they have a long shelf life. As a result the compounds are amenable to commercial production in a scaled-up process.

In one embodiment, the instant invention resides in acetylene-terminated quinoxaline compositions which cure by non-volatile addition reactions. The quinoxaline compositions are prepared by reacting an aromatic bis-benzil (V) with an excess of a bis(o-diamine) (VI), thereby providing an ortho-diamino endcapped quinoxaline oligomer (VII) which is then converted to the acetylene endcapped oligomer (VIII) by reacting with an acetylenic benzil (I). The reactions that occur are shown below by the equations in which the Roman numerals refer to the compositions mentioned in the preceding sentence.

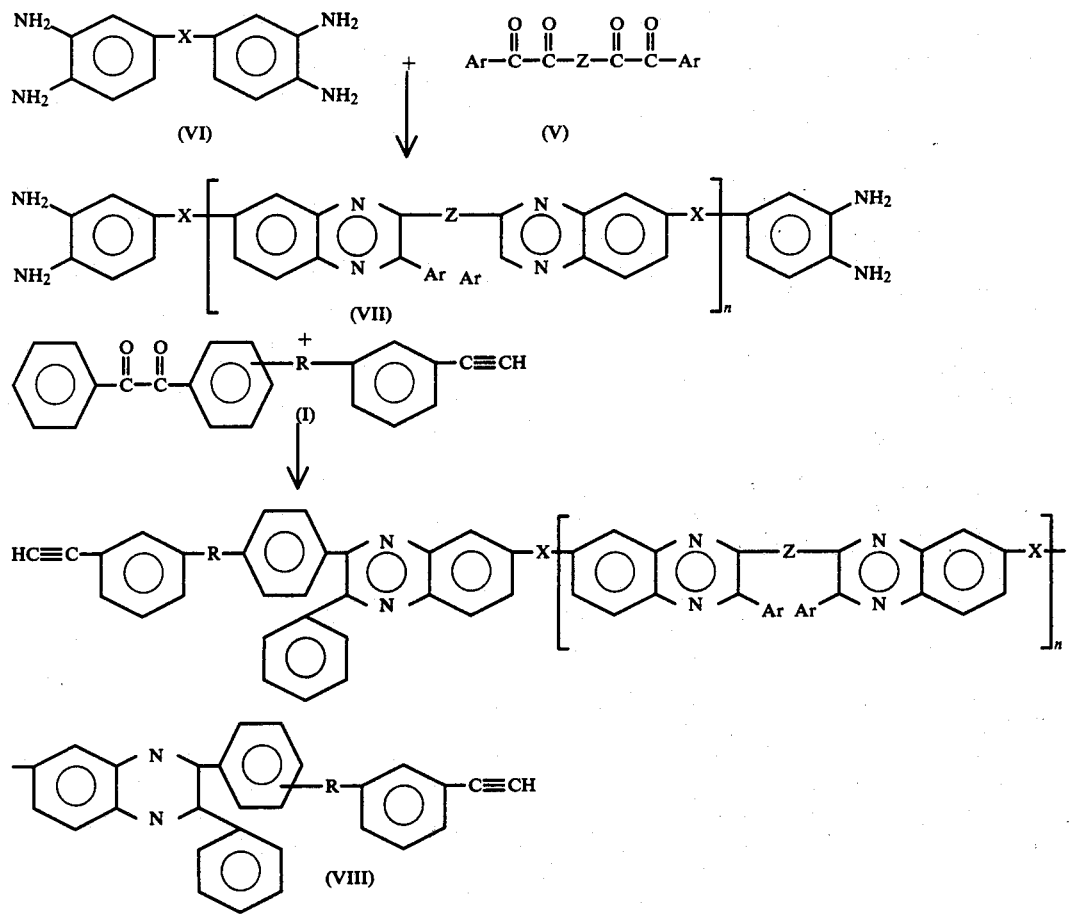

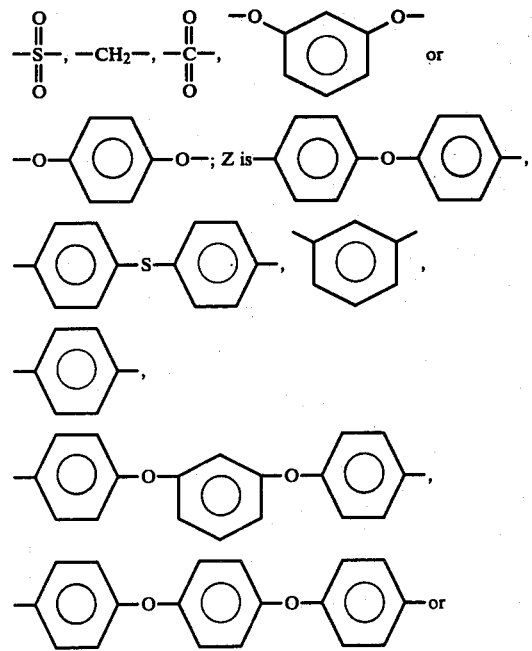

In the foregoing formulas, X is a single bond, —O—, —S—, $-\overset{O}{\underset{O}{S}}-$, —CH$_2$—, $-\overset{O}{\underset{}{C}}-$,

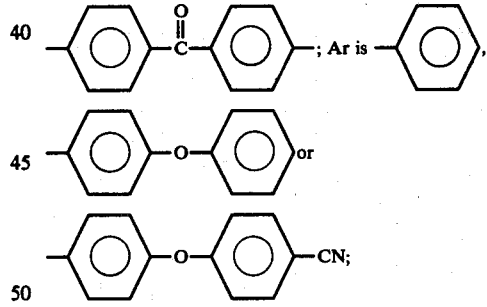

and R is as indicated above. The letter n is an integer indicating the number of recurring units and is usually in the range of 1 to 20, inclusive.

The bis(o-diamines) and the aromatic bisbenzils utilized in preparing the quinoxaline compositions are well known compounds that are described in the literature. Examples of bis(o-diamines) include 3,3'-diaminobenzidine; 3,3', 4,4'-tetraaminodiphenylether; 3,3', 4,4'-tetraaminodiphenylsulfide; 3,3', 4,4'-tetraaminodiphenylsulfone; 3,3'-4,4'-tetraaminodiphenylmethane; 3,3', 4,4'-tetraaminobenzophenone; 1,3-bis(3,4-diaminophenoxy)-benzene; and 2,2'-bis(3,4-diaminophenoxy)-giphenyl. Examples of aromatic bisbenzils include 4,4'-(phenylglyoxaloyl)diphenylether; 1,3-(phenylglyoxaloyl)benzene; 4,4'-(phenylglyoxaloyl)diphenylsulfide; 1,3-bis(4-phenoxyphenylglyoxaloyl)benzene; and 1,4-bis[4-(phenylglyoxaloyl)phenoxy]benzene.

As indicated above, in the first step of preparing the acetylene-terminated quinixaline compositions, an aromatic bisbenzil is reacted with an excess of a bis(o-diamine). Usually, from about 0.10 to 1 mole of the bis(o-diamine) is reacted with 2 moles of the bisbenzil. When the mole ratio of bis(benzil) to bis(o-diamine) is 2 to 1, the value of n in the above equation is 1. As the ratio increases, i.e., greater amounts of bisbenzil as compared to bis(o-diamine) are used, the value of n in the equation also increases. The number of moles of acetylenic benzil endcapping agent used in the second step of the process is generally about equal to the number of moles of the bis(o-diamine) utilized in the first step. It is within the purview of the inventin, however, to employ a molar excess of the endcapping agent, e.g., 1 to 1.25 moles of endcapping agent per mole of bis(o-diamine).

In conducting the process, m-cresol is employed as the reaction medium. The amount of m-cresol used is that which is sufficient to provide a stirrable mixture and can be readily determined by those skilled in the art. The temperatures at which the reactions are carried out usually fall in the range of 80° to 150° C. The total period for the reactions generally ranges from about 30 minutes to 4 hours. The reactions are conducted under a blanket of an inert gas, such as nitrogen, argon or helium.

At the end of the reaction period, the oligomer is recovered and purified by a general procedure that is conventionally followed in solution polymerization processes. Thus, the reaction mixture is cooled, e.g., to about room temperature, after which it is poured into a non-solvent for the oligomer, thereby causing it to precipitate from solution. An alcohol, such as methanol, is conveniently used as the non-solvent. The precipitated oligomer is separated from the liquid by any suitable means, such as by filtration or decantation. After washing the separated oligomer with a non-solvent, it is then dissolved in a solvent, such as tetrahydrofuran, and again precipitated from solution by pouring into a non-solvent. After separation of the precipitated oligomer, it is dried by heating under a vacuum. This procedure can be repeated one or more times in order to further purify the product.

The acetylene-terminated quinoxaline oligomers are readily cured by heating in an inert or oxidative atmosphere at a temperature ranging from about 200° to 370° C. A heating period of from about 1 to 2 hours is usually sufficient to obtain a complete cure. However, longer times, e.g., up to 24 hours, can be used.

A more complete understanding of the invention can be obtained by referring to the following illustrative examples which are not intended, however, to be unduly limitative of the invention.

EXAMPLE I 4-(3-Ethynylphenoxy)benzil

To 100 ml of anhydrous methanol was added 20 g (0.073 mole) of 3-ethynylphenyl(p-toluenesulfonate) and 8.19 g (0.146 mole) of potassium hydroxide. The mixture was heated to reflux under a nitrogen atmosphere and maintained at reflux for 4 hours. A distillation apparatus was attached to the flask, and methanol was distilled from the flask until the residue approached dryness. Then, 400 ml of anhydrous benzene was added, and distillation was continued until 200 ml of benzene was removed. The reaction mixture was freeze dried under reduced pressure, leaving a dry, white powder. The white powder was dissolved in 150 ml of dimethylsulfoxide and transferred to an addition funnel under nitrogen. The solution was added over a 60 minute period to a solution of 4-nitrobenzil (18.6 g, 0.073 mole) in dimethylsulfoxide (300 ml) and stirred at 90° C. under nitrogen. When addition was completed, the reaction mixture was stirred overnight at 23° C. and poured into a solution of sodium hydroxide (50 g) in ice water (1 liter). Extraction with toluene (3 × 50 ml) followed by chromatography on silica gel with benzene as eluent gave 15.4 g (65% yield) of 4-(3-ethynylphenoxy)benzil as a yellow oil which solidified upon standing overnight at 23° C. into a pale yellow solid (m.p. 79°–81° C.).

Analysis Calc'd for $C_{22}H_{14}O_3$, %: C,80.97; H,4.32. Found: C,80.40; H,4.00.

EXAMPLE II

Oligomer prepared from 3,3'-Diaminobenzidine, 4,4'-Bis(phenylglyoxaloyl)diphenylether, and 4-(3-Ethynylphenoxy)benzil A solution of 3,3'-diaminobenzidine (0.41 g, 0.0019 mole) in m-cresol (10 ml) was stirred under nitrogen at 90° C. while a previously deaerated solution of 4,4'-bis(phenylglyoxaloyl)diphenylether (0.41 g, 0.00094 mole) in m-cresol (10 ml) was added over a 10 minute period. The mixture was heated at 90°–100° C. for 2 hors and then 4-(3-ethynylphenoxy)benzil (0.69 g, 0.0021 mole) was added. After an additional hour of heating at 90°–100° C., the reaction mixture was cooled to 23° C. and poured into stirring methanol (300 ml). The yellow precipitate which formed was filtered, washed thoroughly with methanol, reprecipitated twice from tetrahydrofuran by methanol, and dried under vacuum at 60° C. to afford 0.94 g (73%) of oligomer. The structure of the oligomer was characterized by its method of preparation, NMR analysis and elemental analysis. The material softened at 145° C. and, after a 6-hour cure under nitrogen at 280° C., showed a glass transition temperature at 310° C.

EXAMPLE III

Oligomer prepared from 3,3'-Diaminobenzidine, 1,3-Bis(phenylglyoxaloyl)benzene, and 4-(3-Ethynylphenoxy)benzil.

The procedure of Example II was repeated, utilizing 0.42 g (0.0020 mole) of 3,3'-diaminobenzidine, 0.34 g (0.00094 mole) of 1,3-bis(phenylglyoxaloyl)benzil and 0.70 g (0.0022 mole) of 4-(3-ethynylphenoxy)benzil to afford 0.86 g (72%) of oligomer. The structure of the oligomer was characterized by its method of preparation, NMR analysis and elemental analysis. The material softened at 145° C. and, after a 6-hour cure under nitrogen at 280° C., showed a Tg at 310° C.

EXAMPLE IV

Oligomer prepared from 3,3'-Diaminobenzidine, 4,4'-Bis(phenylglyoxaloyl)diphenylsulfide, and 4-(3-Ethynylphenoxy)benzil.

The procedure of Example II was repeated, utilizing 0.49 g (0.0019 mole) of 3,3'-diaminobenzidine, 0.42 g (0.00094 mole) of 4,4'-bis(phenylglyoxaloyl)diphenylsulfide, and 0.66 g (0.0020 mole) of 4-(3-ethynylphenoxy)benzil to afford 0.82 g (60%) of oligomer. The structure of the oligomer was characterized by its method of preparation, NMR analysis and elemental analysis. The material softened at 160° C. and, after a 6-hour cure under nitrogen at 280° C., showed a Tg at 309° C.

EXAMPLE V

Oligomer prepared from 3,3'-Diaminobenzidine, 1,3-Bis(4-phenoxyphenylglyoxaloyl)benzene, and 4-(3-Ethynylphenoxy)benzil.

The procedure of Example II was repeated, utilizing 0.43 g (0.0020 mole) of 3,3'-diaminobenzidine, 0.53 g (0.0010 mole) of 1,3-bis(4-phenoxyphenylglyocaloyl)benzene, and 0.72 g (0.0022 mole) of 4-(3-ethynylphenoxybenzil to afford 0.87 g (57%) of oligomer. The structure of the oligomer was characterized by its method of preparation, NMR analysis and elemental analysis. The material softened at 145° C. and, after a 6-hour cure under nitrogen at 280° C., showed a Tg at 275° C.

EXAMPLE VI

Oligomer prepared from 3,3'-Diaminobenzidine, 1,4-Bis[4-(phenylglyoxaloyl)phenoxy]benzene, and 4-(3-Ethynylphenoxy)benzil.

The procedure of Example II was repeated, utilizing 0.34 g (0.0016 mole) of 3,3'-diaminobenzidine, 0.42 g (0.00082 mole) of 1,4-bis[4-phenylglyoxaloyl)phenoxy]benzene, and 0.57 g (0.0018 mole) of 4-(3-ethynylphenoxy)benzil to give 1.0 g (83% yield) of oligomer. The structure of the oligomer was characterized by the method of preparation, NMR analysis and elemental analysis. The material softened at 150° C. and, after a 6-hour cure under nitrogen at 280° C., showed a Tg at 322° C.

EXAMPLE VII

Oligomer prepared from 3,3',4,4'-Tetraaminodiphenylether, 4,4'-Bis(phenylglyoxaloyl)diphenylether and 4-(3-Ethynylphenoxy)benzil.

The procedure of Example II was repeated, utilizing 0.43 g (0.001 mole) of 4,4'-bis(phenylglyoxaloyl)diphenylether, 0.46 g (0.002 mole) of 3,3',4,4'-tetraaminodiphenylether and 0.65 g (0.002 mole) of 4-(3-ethynylphenoxy)benzil to give 1.2 g (86% yield) of oligomer. The oligomer was characterized by its method of preparation, NMR analysis and elemental analysis. The material softened at 143° C. and, after a 6-hour cure under nitrogen at 280° C., showed a TG at 298° C.

EXAMPLE VIII

Oligomer prepared from 3,3',4,4'-Tetraaminodiphenylether, 1,3-Bis(phenylglyoxaloyl)benzene, and 4-(3-Ethynylphenoxy)benzil.

The procedure of Example II was repeated, utilizing 0.34 g (0.001 mole) of 1,3-bis(phenylglyoxaloyl)benzene, 0.46 g (0.002 mole) of 3,3',4,4'-tetraaminodiphenylether, and 0.65 g (0.002 mole) of 4-(3-ethynylphenoxy)benzil to give 1.2 g (84% yield) of oligomer. The structure of the oligomer was characterized by its method of preparation, NMR analysis and elemental analysis. The material softened at 145° C. and, after a 6-hour cure under nitrogen at 280° C., exhibited a Tg at 290° C.

EXAMPLE IX

Oligomer prepared from 3,3',4,4'-Tetraaminodiphenylether, 1,3-Bis(4-phenoxyphenylglyoxaloyl)benzene, and 4-(3-Ethynylphenoxy)benzil.

The procedure of Example II was repeated, utilizing 0.52 g (0.001 mole) of 1,3-bis(4-phenoxyphenylglyoxaloyl)benzene, 0.46 g (0.002 mole) of 3,3',4,4'-tetraaminodiphenylether and 0.65 g (0.002 mole) of 4-(3-ethynylphenoxy)benzil to give 1.2 g (80% yield) of oligomer. The structure of the oligomer was characterized by its method of preparation, NMR analysis and elemental analysis. The material softened at 125° C. and, after a 6-hour cure under nitrogen at 280° C., showed a Tg at 257° C.

Properties of the cured oligomers prepared in the preceding examples are summarized in the table set forth below.

TABLE
Summary of Oligomer Properties

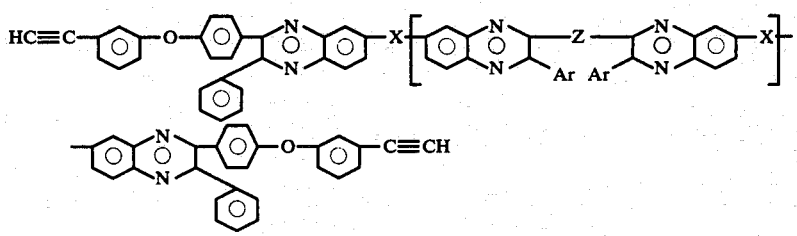

| Example No. | X | Z | Ar | Softening Pt, °C. | Tg, °C.[1] |
|---|---|---|---|---|---|
| II | —[2] | –⌬–O–⌬– | –⌬– | 145 | 310 |
| III | — | –⌬– | –⌬– | 145 | 310 |
| IV | — | –⌬–S–⌬– | –⌬– | 160 | 309 |
| V | — | –⌬– | –⌬–O–⌬– | 145 | 275 |
| VI | — | –⌬–O–⌬–O–⌬– | –⌬– | 150 | 322 |

TABLE-continued
Summary of Oligomer Properties

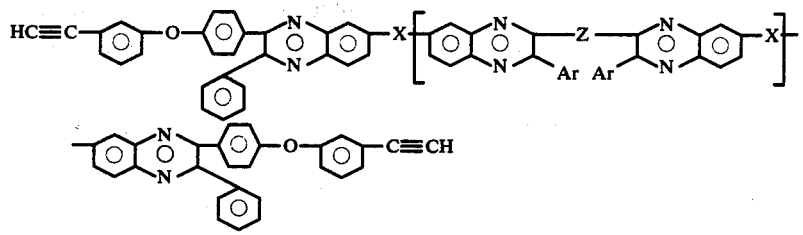

| Example No. | X | Z | Ar | Softening Pt, °C. | Tg, °C.[1] |
|---|---|---|---|---|---|
| VII | —O— | —⌬—O—⌬— | ⌬ | 143 | 298 |
| VIII | —O— | ⌬ (meta) | ⌬ | 145 | 290 |
| IX | —O— | ⌬ (meta) | ⌬—O—⌬ | 125 | 257 |

[1]Glass transition temperature of the cured oligomer after 6 hours at 280° C. under nitrogen atmosphere.
[2]Single bond.

The foregoing data demonstrate that the acetylene-terminated benzils of this invention make it possible to provide acetylene terminated phenylquinoxaline oligomers which can be cured by addition reactions in a short period of time. The curing mechanism eliminates the problem of by-product evolution so that voids are not formed in the cured products. The cured oligomers are thermally stable having a high glass transition temperature, an important property for materials which may be subjected to high temperatures.

The acetylene terminated quinoxaline compositions are very soluble in low boiling solvents, such as methylene chloride, tetrahydrofuran and dioxane. This property of the oligomers makes them eminently suitable for use in the fabrication of solvent-free prepregs and void-free structural components. The low softening points of the oligomers make it possible to employ low processing temperatures in the manufacture of structural reinforced composites. Of primary importance, the acetylenic benzils used as endcapping agents have a long shelf life, a property which makes it feasible to employ the quinoxaline compositions in a scaled-up process for fabricating composites.

As will be evident to those skilled in the art, modifications of the present invention can be made in view of the foregoing disclosure without departing from the spirit and scope of the invention.

We claim:
1. An acetylene terminated quinoxaline composition having the following formula:

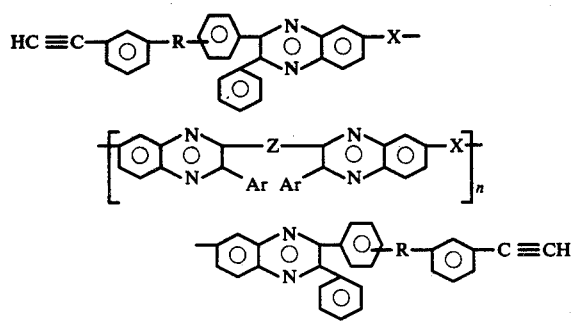

wherein X is a single bond, —O—, —S—, $$-\overset{O}{\underset{O}{\overset{\|}{S}}}-, -CH_2-, -\overset{O}{\underset{\|}{C}}-,$$

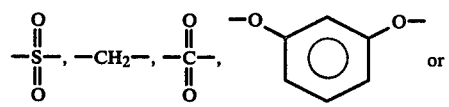

; Z is

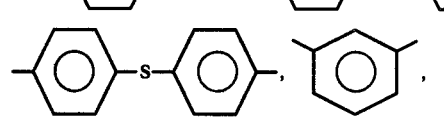

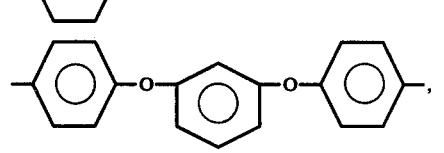

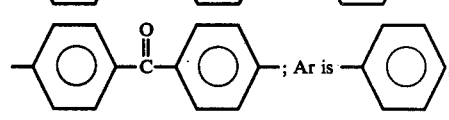

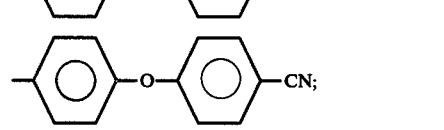

; Ar is

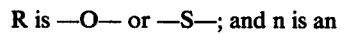

R is —O— or —S—; and n is an integer ranging from 1 to 20, inclusive.

2. The composition according to claim 1 in which X is a single bond, Z is

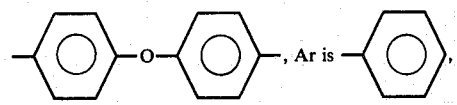
and R is —O—.
3. The composition according to claim 1 in which X is a single bond, Z is
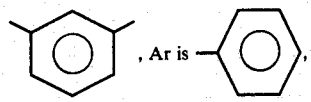
and R is —O—.
4. The composition according to claim 1 in which X is a single bond, Z is
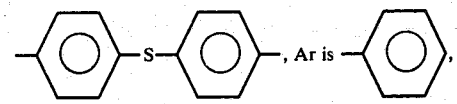
and R is —O—.
5. The composition according to claim 1 in which X is a single bond, Z is
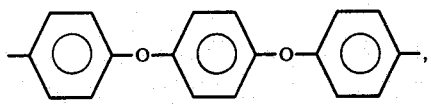
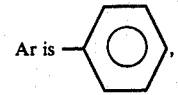
and R is —O—.
6. The composition according to claim 1 in which X is —O—, Z is
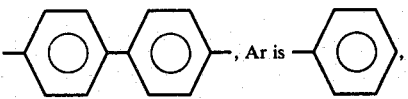
and R is —O—.
* * * * *